(12) United States Patent  
Rizvi

(10) Patent No.: US 8,012,166 B2  
(45) Date of Patent: Sep. 6, 2011

(54) LAPAROSCOPIC INSTRUMENT TIP AND METHOD OF SPECIMEN COLLECTION

(75) Inventor: Syed Rizvi, Bakersfield, CA (US)

(73) Assignee: Centum Research LLC, Bakersfield, CA (US)

( * ) Notice: Subject to any disclaimer, the term of this patent is extended or adjusted under 35 U.S.C. 154(b) by 1404 days.

(21) Appl. No.: 11/428,836

(22) Filed: Jul. 6, 2006

(65) Prior Publication Data

US 2008/0009858 A1    Jan. 10, 2008

(51) Int. Cl.  
*A61B 17/00* (2006.01)

(52) U.S. Cl. ............ 606/205; 606/48; 606/51; 606/206; 600/564

(58) Field of Classification Search .......... 600/562, 600/564–567; 128/898; 606/37–52, 167, 606/170, 205–208  
See application file for complete search history.

(56) References Cited

U.S. PATENT DOCUMENTS

| | | |
|---|---|---|
| 3,938,527 A | 2/1976 | Rioux |
| 3,967,625 A | 7/1976 | Yoon |
| 4,226,239 A | 10/1980 | Polk |
| 4,374,523 A | 2/1983 | Yoon |
| 4,655,216 A | 4/1987 | Tischer |
| 5,300,081 A | 4/1994 | Young |
| 5,352,235 A | 10/1994 | Koros |
| 5,397,325 A * | 3/1995 | Della Badia et al. ......... 606/144 |
| 5,575,802 A | 11/1996 | McQuilkin |
| 5,578,052 A | 11/1996 | Koros |
| 5,746,740 A * | 5/1998 | Nicholas ......................... 606/52 |
| 5,797,927 A * | 8/1998 | Yoon ............................. 606/144 |
| 5,833,696 A | 11/1998 | Whitfield |
| 6,041,679 A * | 3/2000 | Slater et al. .................. 76/104.1 |
| 6,112,747 A | 9/2000 | Jones |
| 6,152,923 A | 11/2000 | Ryan |
| 6,241,740 B1 | 6/2001 | Davis |
| 6,309,384 B1 | 10/2001 | Harrington |
| D457,958 S | 5/2002 | Dycus |
| 6,682,528 B2 | 1/2004 | Frazier |
| 6,840,938 B1 | 1/2005 | Morley |
| 6,913,579 B2 | 7/2005 | Truckai |
| 6,929,644 B2 | 8/2005 | Truckai |
| 6,932,810 B2 | 8/2005 | Ryan |
| 6,960,210 B2 | 11/2005 | Lands |
| 7,857,827 B2 * | 12/2010 | Measamer .................... 606/205 |
| 2005/0149016 A1 * | 7/2005 | Rizvi .............................. 606/51 |

* cited by examiner

*Primary Examiner* — Ahmed M Farah

(57) ABSTRACT

A unique laparoscopy instrument tip and method which allows simultaneous gasping, cauterization, dissection, containment, enclosure and removal of body tissue. Mechanisms for grasping, holding, manipulating, cauterizing, dissecting, encasement in an enclosed cavity and removing the tissue are provided in one implement allowing easy, safe and quick performance of the procedure.

4 Claims, 1 Drawing Sheet

LAPAROSCOPIC INSTRUMENT TIP AND METHOD OF SPECIMEN COLLECTION

FIELD OF THE INVENTION

This invention relates to a laparoscopy instrument tip and method of use thereof, which prevents slippage of the tissue and allows simultaneous manipulation, cauterization, dissection and encasement of the tissue prior to the removal from the body.

STATEMENT OF THE INVENTION

A unique laparoscopy instrument tip and method, which allows simultaneous manipulation, cauterization, dissection, encasement and removal of the body tissue. The tip is located at the distal end of the instrument, which allows lifting and grasping the tissue, cauterizing, cutting and encasing it. The raised outer edge of the fixed lower jaw prevents the slippage of the tissue during the procedure. The ring shape jaw allows cauterizing the tissue. The cup shape part dissects and protects the tissue until it is removed. The tip can be used on any part of the body where simultaneous manipulation, cauterization, tissue dissection and protected removal of the dissected tissue are desired. Any mechanism on the laparoscopy device can be used to open/close the jaws, manipulate the device and to operate the cautery/cutting mechanisms. The sources of energy used include but are not limited to electrical, ultrasonic, laser or radio energy.

The tip can be permanent or a disposable modular laparoscopic instrument tip. Disposable modular tip can provide surgical efficiency, convenience, precision, durability and cost effectiveness by replacing only the disposable modular tip and reusing the non-disposable laparoscopy instrument.

BACKGROUND OF THE INVENTION

Technical advances, particularly the use of the laparoscopy, have significantly affected the setting in which procedures can be performed. Several laparoscopic instruments have been described in prior art. Many of these instruments provide multifunctionality such as simultaneous grasping, coagulation and cutting of the tissue. Slippage of the tissue from the tip is a problem during laparoscopic surgeries. It is difficult to hold the tissue for cautery or cutting adding to the technical difficulties, frustration, operating time, cost and risk of complications. Laparoscopic instrumentation in prior art does not provide for the prevention of the slippage of the tissue from the tip. Furthermore prior art does not provide for complete encasement and containment of the dissected tissue along with the cautery and active cutting mechanism before the removal. Lack of instrumentation and methods of preventing slippage of the tissue during the procedure and lack of adequate all in one cautery, cutting and containment mechanism prior to removal make it challenging for surgeons to perform operations using minimally invasive techniques.

During unipolar cautery, which can be performed with or without the laparoscopic instrument, patient's body is part of the circuit. This method has been associated with dangerous and fatal consequences due to injuries to other organs.

The bipolar cautery technique is the safest and simplest to perform. The poles of the tip of the instrument conduct the electricity between them, with no current flow beyond the instrument tip, so the patient is not part of the circuit eliminating the risk of injury to other organs.

Tischer (U.S. Pat. No. 4,655,216) is a surgical combination instrument for grasping tissue, coagulating it and removing the tissue between the coagulated areas. This device does not provide for a mechanism to prevent the slippage of the tissue. This device also does not provide for complete encasement of the dissected tissue.

Ryan (U.S. Pat. No. 6,152,923) device is merely a grasping bipolar forecep with active passive cutting mechanism, which does not provide for preventing the slippage of the tissue. This device also does not provide for complete encasement of the dissected tissue. Furthermore this device does not provide an independent cutting mechanism.

Lands (U.S. Pat. No. 6,960,210) described a laparoscopic bipolar electrosurgical instrument that can just apply a large closure force between its jaw.

Ryan (U.S. Pat. No. 6,932,810) described an axial elongate bipolar tissue sealer/cutter.

Truckai (U.S. Pat. No. 6,929,644) described a working end of a surgical instrument that carries first and second jaws for delivering energy to tissue.

Truckai (U.S. Pat. No. 6,913,579) described an electrosurgical working end and method for obtaining a tissue sample for biopsy purposes with curved jaw members that are positioned on opposing sides.

Morley (U.S. Pat. No. 6,840,938) described a bipolar surgical instrument that includes opposing grips that can engage the tissue.

Frazier (U.S. Pat. No. 6,682,528) described an endoscopic bipolar forceps for clamping and sealing tissue includes first and second jaw members pivotally attached in opposing relation.

Dycus (U.S. Pat. D457,958) described a vessel sealer and divider.

Rioux (U.S. Pat. No. 3,938,527) described a laparoscopic electrocautery instrument for tubal cauterization.

Yoon (U.S. Pat. No. 3,967,625) described a method for sterilizing the female by tubal ligation comprising the use of a ring and an applicator device.

Polk (U.S. Pat. No. 4,226,239) described a surgical ligating instrument for tubal ligation by the application of two or more elastic rings.

Yoon (U.S. Pat. No. 4,374,523) describes a two cylinder ring applicator device and method for applying an elastic occluding ring on fallopian tubes.

Young (U.S. Pat. No. 5,300,081) describes an apparatus for applying surgical clips on the fallopian tubes.

Koros (U.S. Pat. No. 5,352,235) describes a monopolar laparoscopic instrument with scissor like blades to cut the tissue.

McQuilkin (U.S. Pat. No. 5,575,802) described a clip suitable for sexual sterilization.

Koros (U.S. Pat. No. 5,578,052) describes insulated laparoscopic grasper with removable shaft.

Whitfield (U.S. Pat. No. 5,833,696) described a surgical clip applying instrument.

Jones (U.S. Pat. No. 6,112,747) describes a method of female sterilization with the application of laser energy through the hysteroscope.

Davis (U.S. Pat. No. 6,241,740) describes an instrument and method for ligating with a clip and cutting the tissue.

Harrington (U.S. Pat. No. 6,309,384) describes a method, which involves thermally damaging the lining of the uterotubal junction followed by placement of a foam plug.

It is therefore an object of the present invention to provide a tip for a bipolar laparoscopic instrument, which prevents the tissue from slippage during the procedure.

Another object is to provide a mechanism for the containment of the dissected tissue by complete encasement in an enclosed cavity during removal from the body.

A further object of the invention is provision of a multi-function tip for the bipolar laparoscopic instrument, which allows simultaneous cautery, dissection and retention of the dissected tissue in an enclosed cavity.

SUMMARY

A unique laparoscopy instrument tip and method which allows simultaneous gasping, cauterization, dissection, containment, enclosure and removal of body tissue. Mechanisms for grasping, holding, manipulating, cauterizing, dissecting, encasement in an enclosed cavity and removing the tissue are provided in one implement allowing easy, safe and quick performance of the procedure.

BRIEF DESCRIPTION OF THE DRAWINGS

Without restricting the full scope of this invention, the preferred form of this invention is illustrated in the following drawings.

DESCRIPTION OF THE PREFERRED EMBODIMENT

Figure 1:
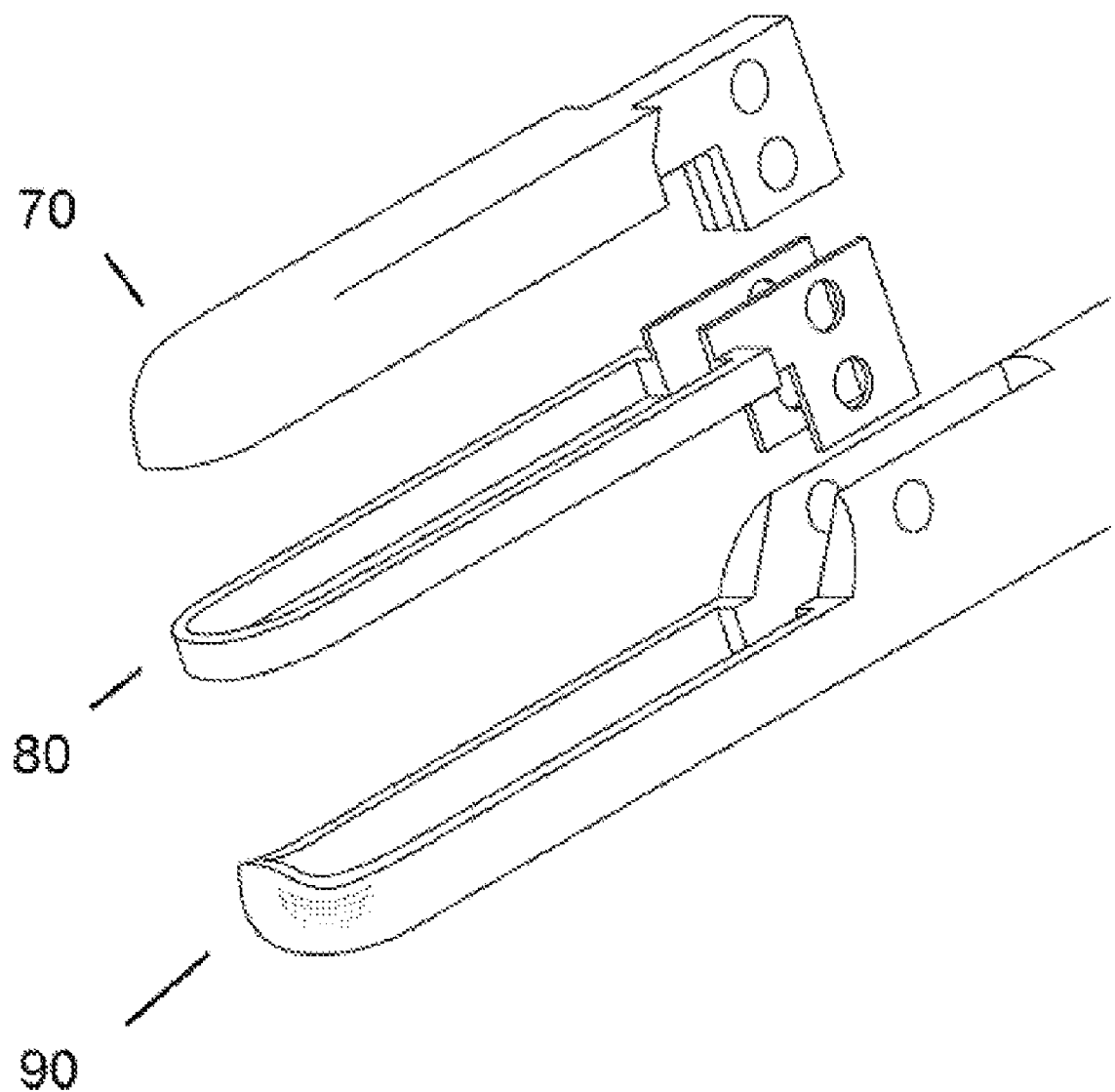
FIG. 1 shows the overview of all components of the tip.

FIG. 1 shows the overview of all components of the tip.

The cup shape movable cutting jaw 70 is connected to the handle of the laparoscopy instrument. This movable cutting part of the tip is approximately 1.5 centimeters long. This part can be opened or closed by operating the handle and functions to dissect and encase the dissected tissue along with the fixed jaw 90.

The cautery ring 80 is connected to the handle of the laparoscopic instrument. This ring can be opened or closed by operating the handle and is attached to the bipolar electrical circuit. Total length of this part is approximately 2.2 centimeters.

The fixed jaw 90 is connected to the shaft of the laparoscopic instrument and is approximately 2.2 centimeters long. This jaw is also attached to the bipolar electrical circuit. This part is fixed to the instrument and cannot be opened or closed by operating the handle but functions to dissect and encase the dissected tissue along with the movable cutting jaw 70.

The preferred diameter of the tip is 7 millimeters. Fixed lower jaw 90 is 7 millimeters wide. Ring shape cautery jaw 80 is 7 millimeters wide and the cup shape movable cutting jaw 70 is 5 millimeters wide. Difference in the width of the ring shape cautery jaw 80 and cup shape cutting jaw 70 allows for at least one-millimeter margin.

OPERATION OF THE INVENTION

Jaws of the tip device are opened. Tissue is grasped assuring that the entire tissue is in the jaws of the device. The cauterizing jaw is closed.

The surgeon then actuates the bipolar cautery and cauterizes the tissue. The surgeon than engages the cutting mechanism until the tissue is completely dissected and traps the dissected portion of the tissue into the jaws. The cautery jaw is then opened slightly, instrument is pulled back and the jaw is closed. The specimen is removed by pulling the device back and bringing it out of the body. The specimen is retrieved after jaws are opened.

It is to be understood that both the foregoing general description and the following detailed description are exemplary and explanatory but are not restrictive of the invention.

The invention in its broader aspects is not limited to the specific details shown and described, and departures may be made from such details without departing from the principles of the invention and without sacrificing its chief advantages.

What is claimed is:

1. A tip for a bipolar laparoscopy instrument comprising:
    a fixed jaw with a raised outer edge, which is configured to be connected to a power source for bipolar cautery;
    a movable ring shape jaw, which comprises a hollow interior and configured to be connected to a power source for bipolar cautery; and
    a movable cup shape cutting jaw, wherein (a) the movable ring shape jaw and fixed jaw exhibit the same width, (b) the cutting jaw exhibits a width that is less than a width of the ring shape jaw, (c) the ring shape jaw is positioned between the fixed jaw and the cutting jaw, and (d) the fixed jaw and cutting jaw, when in a closed position, are configured to encase and protect dissected tissue until it is removed from a body.

2. A laparoscopy instrument tip as in claim 1, which allows simultaneous manipulation, cauterization, dissection, encasement and removal of an entire specimen of body tissue.

3. A laparoscopy instrument tip as in claim 1, which prevents slippage of body tissue during a laparoscopic procedure.

4. A method of dissecting tissue comprising: grasping the tissue, cauterizing, dissecting, encasing and removing a specimen of tissue with the laparoscopy instrument tip of claim 1.

\* \* \* \* \*